United States Patent [19]

Bogart et al.

[11] Patent Number: 4,665,564
[45] Date of Patent: May 19, 1987

[54] UPPER TORSO GARMENTS

[76] Inventors: Jimmie M. Bogart, 19 New St., Apalachin, N.Y. 13732; Elvina J. Long, 5 Courtly Cir., Owego, N.Y. 13827

[21] Appl. No.: 921,400

[22] Filed: Oct. 22, 1986

[51] Int. Cl.$^4$ .......................... A41B 1/21; A41B 1/00
[52] U.S. Cl. ........................................... 2/119; 2/115; 2/DIG. 7
[58] Field of Search .................... 2/115, 119, 106, 102, 2/108, 105, DIG. 7, 69, 83, 74, 70, 44, 45

[56] References Cited

U.S. PATENT DOCUMENTS 2,850,046  9/1883  Lemos ..................................... 2/115
3,997,982 12/1976  Holland .................................. 2/119

Primary Examiner—Doris L. Troutman
Attorney, Agent, or Firm—Richard G. Stephens

[57] ABSTRACT

A garment to be worn with a cervical traction device includes four detachable slit openings extending from adjacent neck-shoulder areas of the wearer to lower extremities of the garment, allowing the garment to be put on and taken off the wearer.

4 Claims, 9 Drawing Figures

UPPER TORSO GARMENTS

My invention relates to orthopedic upper-torso garments, and more particularly to garments, such as shirts, jackets, blouses, dresses and the like which may be worn by a person on whom an orthopedic cervical traction device commonly termed a "halo" has been installed.

A halo is installed on a person having a broken neck to immobilize the person's head relative to his or her chest. As shown below, a typical halo comprises a rigid vest from which a group of rigid rods extend upwardly, with the upper ends of the rods fastened to the person's head by screws. Some persons are required to wear a halo for many months.

A person installed in a halo necessarily experiences many discomforts, but many wearers of such a device become physically capable of sitting, walking and doing light desk work. However, the inability of a person wearing a halo to wear any ordinary upper-torso clothing has created added discomfort, not only in the sence of body warmth but also that of modesty. A primaary object of the invention is to provide an upper-torso garment which can be worn in conjunction with a halo. The term "upper torso garment" is used herein to mean a garment which covers at least a portion of the neck and shoulders area of the wearer. As will become clear below, the garment also can cover many other areas of the wearer's body, and in essence constitute a full-length dress, if desired. Another object of the invention is to provide a garment which may be applied to lie adjacent the wearer's neck despite the presence of a plurality of rods which extend between the wearer's chest and head.

Some attendant objects of the invention are to provide upper-torso garments wearable with a halo where the garments, when installed on a wearer, closely resemble the appearance of normal or ordinary upper-torso garments, and provide warmth and protection similar to that of ordinary upper-torso garments, and can be laundered or dry-cleaned without difficulty or damage.

Another object is to provide an upper torso garment which can be readily installed on and removed from a person wearing a halo.

The following prior art may be of interest:

| | | |
|---|---|---|
| 776,054 - Glover | 1,489,046 - Thompson | 4,258,440 - McGowan |
| 818,351 - Clark | 3,276,036 - Cator | 4,570,268 - Freeman |

Other objects of the invention will in part be obvious and will in part appear hereinafter.

The invention accordingly comprises the features of construction, combination of elements, and arrangement of parts, which will be exemplified in the constructions hereinafter set forth, and the scope of the invention will be indicated in the claims.

For a fuller understanding of the nature and objects of the invention reference should be had to the following detailed description taken in connection with the accompanying drawings, in which.

Figure 3B:
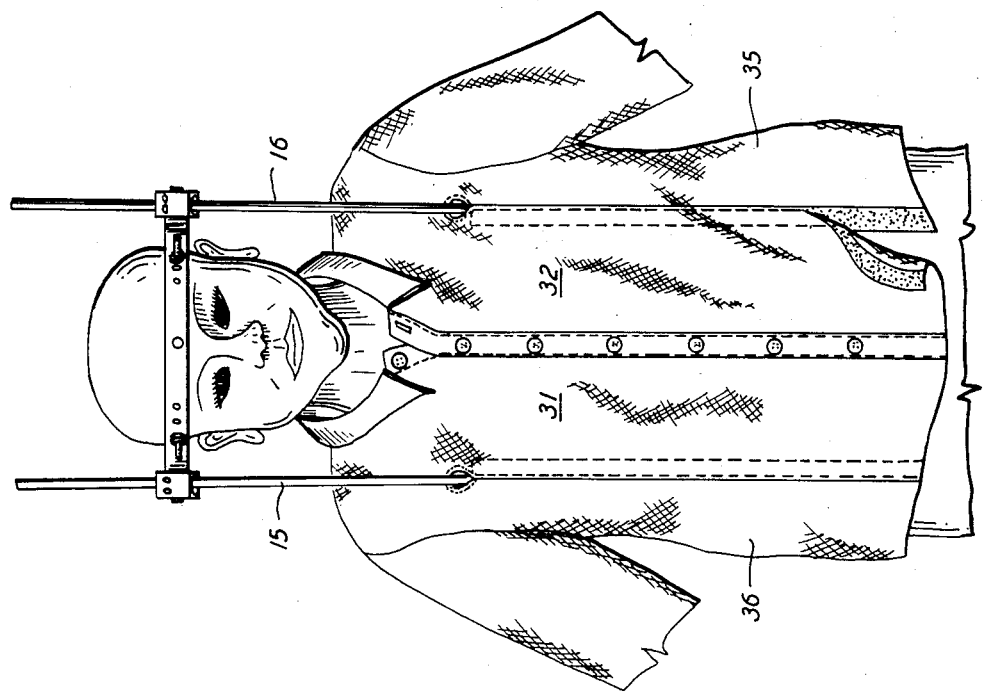
FIGS. 3b, 4b and 5b are front, rear and side elevation views, respectively, illustrating the person with the shirt of FIGS. 1 and 2 installed.
Figure 3A:
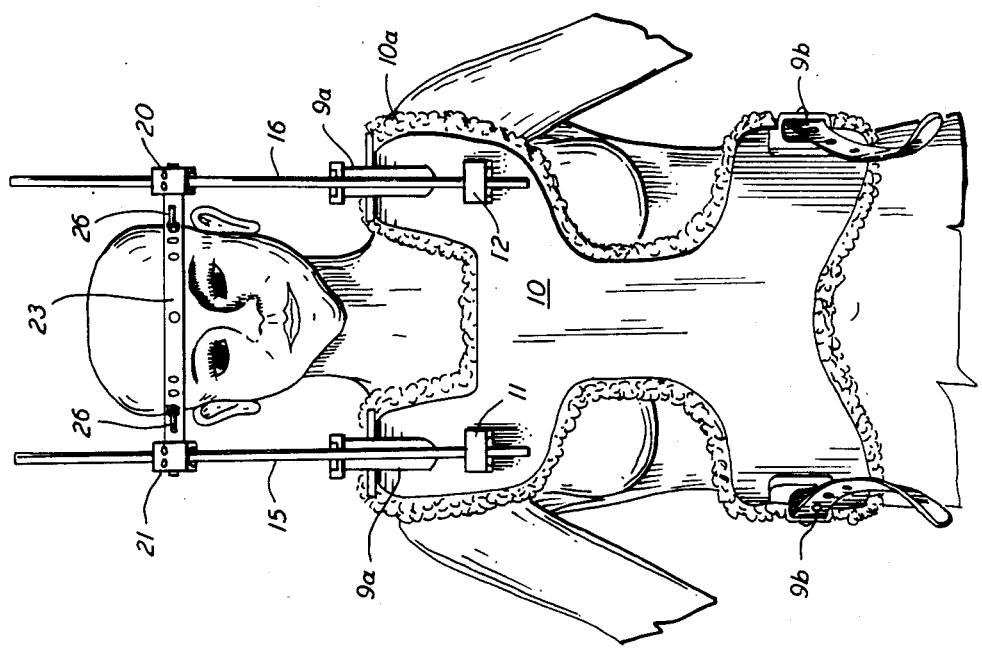
FIGS. 3a, 4a and 5a are front, rear and side elevation views, respectively, illustrating a person wearing a halo assembly and no upper torso garment.
Figure 4B:
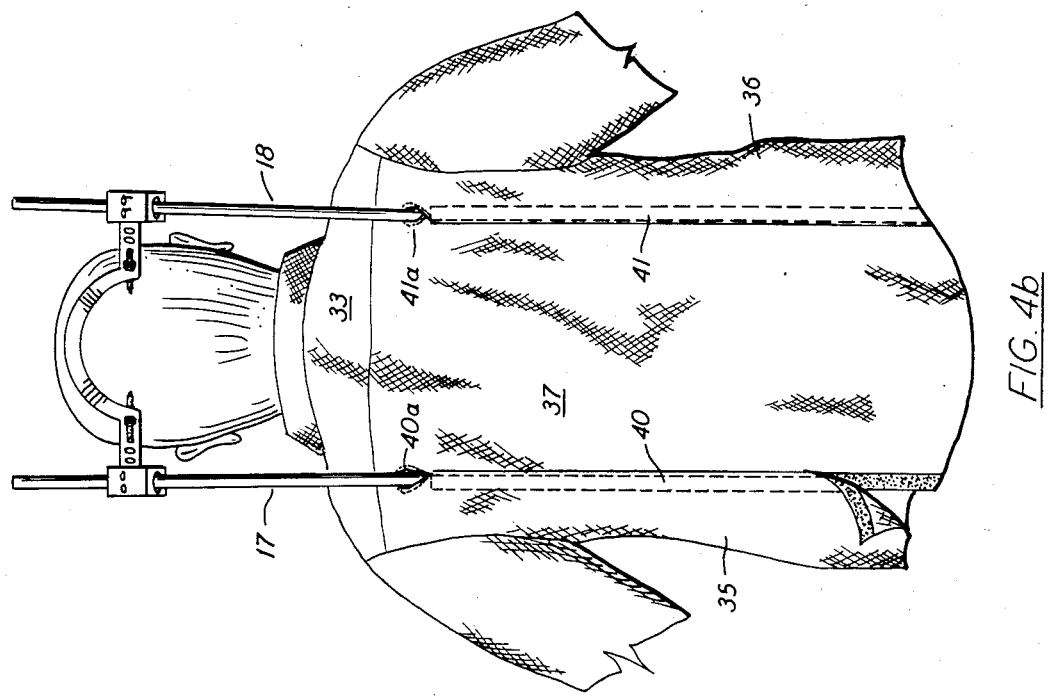
Figure 4A:
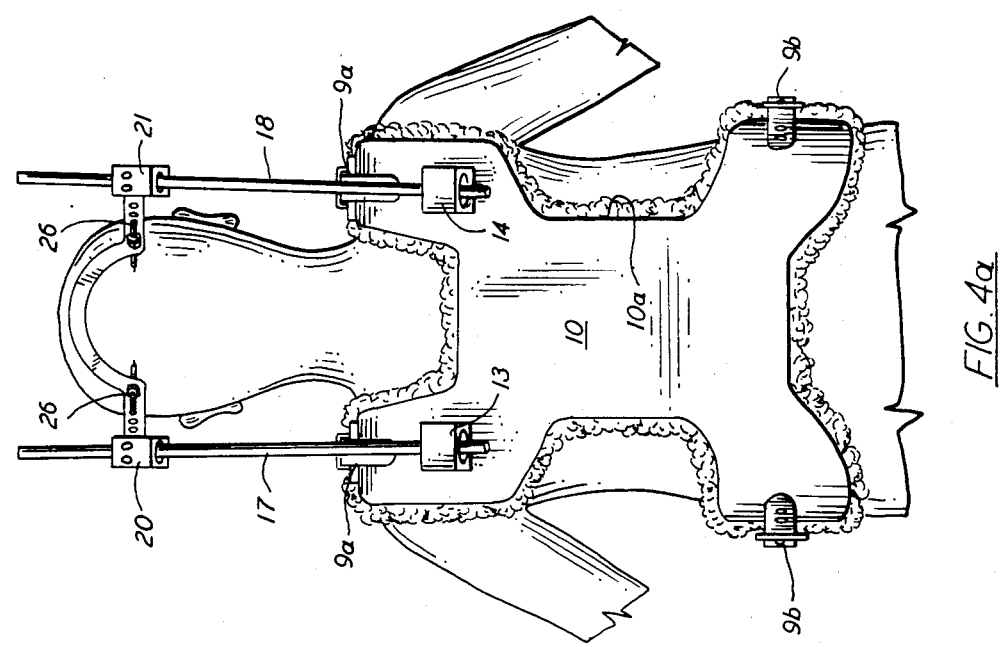
Figure 5B:
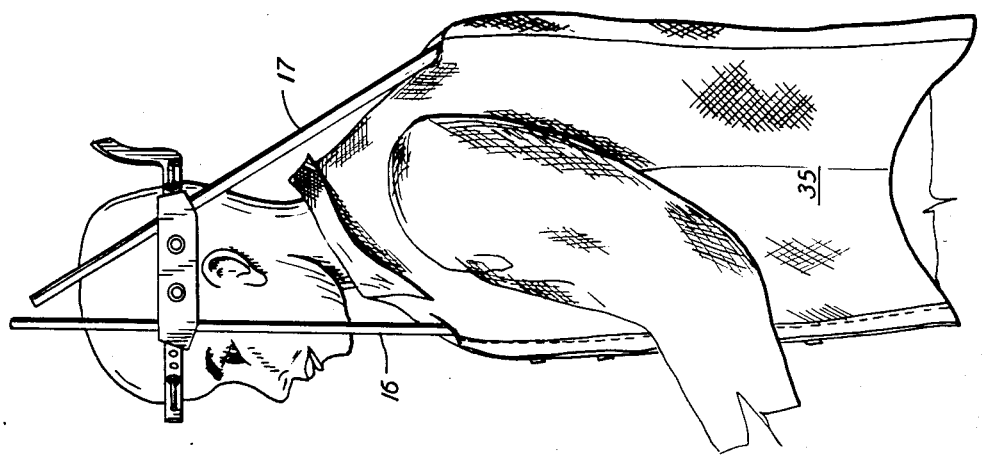
Figure 5A:
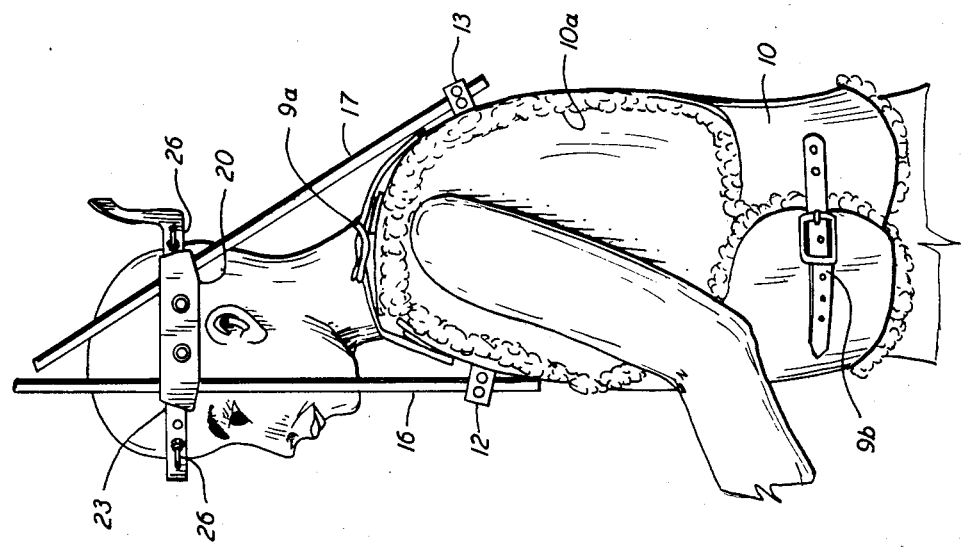

Referring first to FIGS. 3a, 4a and 5a, the halo device will be seen to be a semi-rigid vest 10 formed of plastic, lined with lamb's wool 10a, and tightly strapped to the wearer's upper torso by means of shoulder straps 9a,9a and side straps 9b,9b. Four clamps 11, 12, 13, 14 rigidly affixed to the rigid plastic exterior of vest 10 clamp the lower ends of four rigid rods 15, 16, 17, 18 which extend upwardly past the wearer's head. Brackets 20,21 clamp the upper ends of the rods and support a rigid metal ring 23. A plurality of screws 26,26 (four are often used) extend inwardly from ring 23, piercing the wearer's scalp and engaging his skull, thereby completely immobilizing the neck. One known form of cervical traction device is the PMT-PATIL halo/vest assembly Model 1212 sold by PMI, Inc., Hopkins, Minn. Such a cervical tension device must be installed on a patient and adjusted by a skilled orthopedic surgeon, and it is often necessary that a patient wear the device without interruption for many months. It is completely impermissible to remove such a device from a patient to even bathe the patient, let alone for the purpose of dressing or undressing the patient. It will be apparent that the presence of rods 15–18 extending beside and spaced from the patient's neck precludes covering the patient's neck and shoulders with any normal form of garment. As will be apparent from FIG. 3a, the halo device covers some of the upper torso of the wearer, but leaves many portions exposed, tending to embarrass the wearer of the halo, particularly if the wearer is female. It has been known to attempt to envelope the entire upper torso of such a person in a sheet or blanket, so that the person can receive visitors. The wearer of a halo often finds that strategm unsatisfactory and unnerving, since she or he cannot turn her or his head to determine whether she or he is still decently covered. And the use of a sheet or blanket has been deemed completely impractical for wear while doing desk work or the like.

Figure 1:
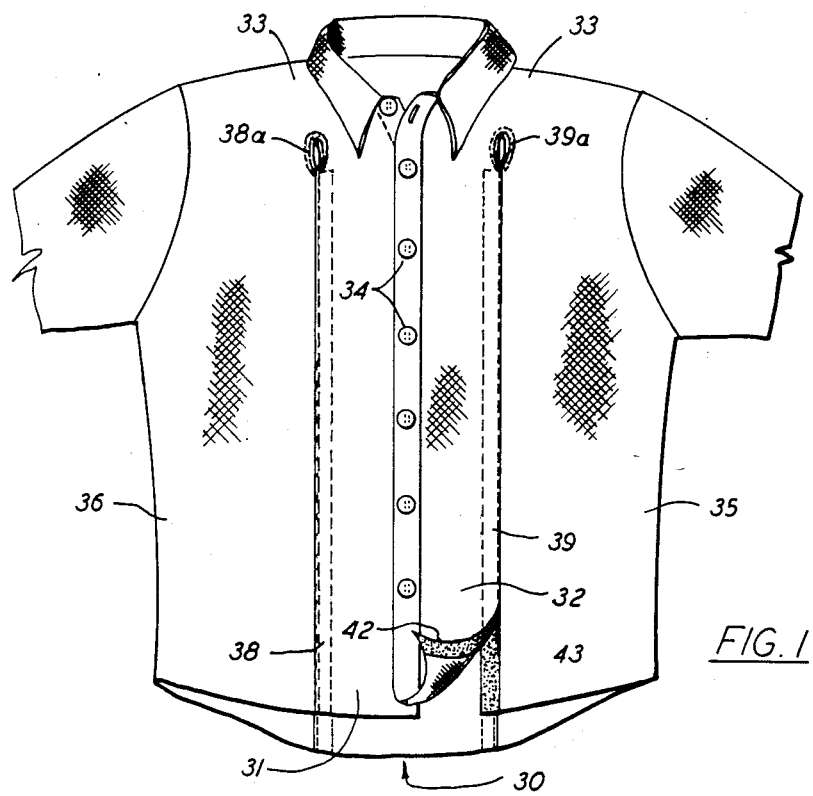
FIG. 1 is a front view of one form of a man's shirt constructed in accordance with the present invention.
Figure 2:
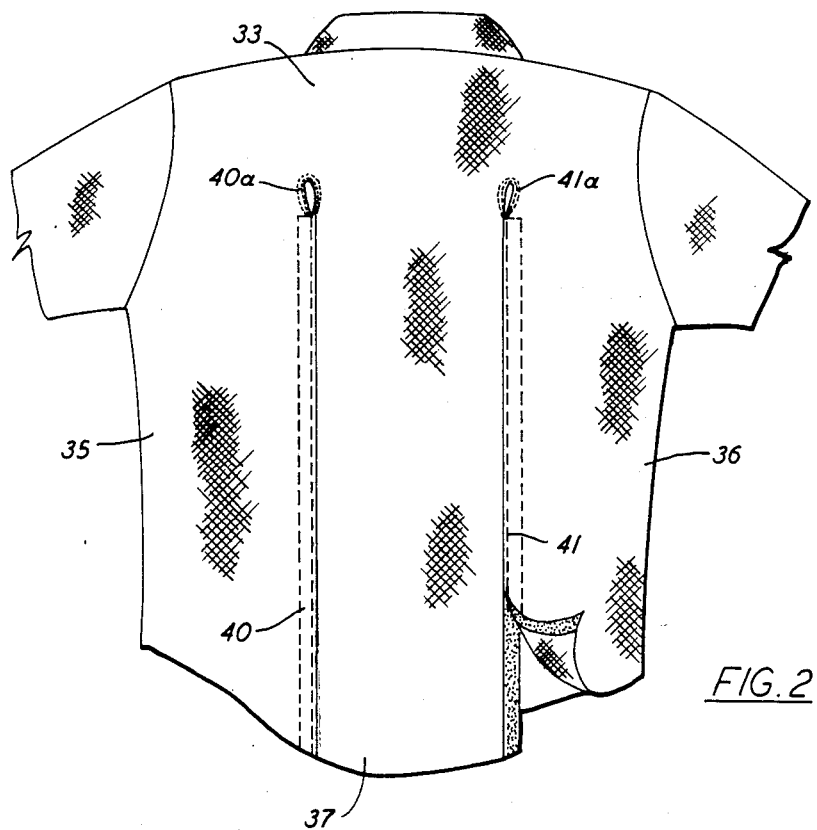
FIG. 2 is a rear view of the garment of FIG. 1.

In accordance with the present invention, and referring now to FIGS. 1 and 2, and to FIGS. 3b, 4b and 5b, I provide an upper torso garment which has a full-length or neck-to-bottom opening 30 resembling or duplicating that of an ordinary shift or blouse. In FIG. 2 the neck-to-bottom opening is formed by the juncture of front panels 31,32, which descend from a neck-encircling or yoke portion 33 of the garment adjacent the shoulders and neck of the wearer. As in typical shirts and blouses, panels 31 and 32 are shown adapted to be fastened together by cooperating buttons 34,34 and button holes. The garment has a pair of side panels 35,36 and a back panel 37 which also descend from yoke portion 33. The shirt of FIGS. 1 and 2 will be seen to be identical to a conventional shirt except that four slits or detachable openings 38–41 have been provided to extend from areas near the neck of the wearer down to the lower extremities of the garment. From adjacent the upper end of each slit to near the lower extremity of the garment, cooperative fastening means are provided to fasten the edges of each slit. For example, a strip of Velcro (trademark) loop-forming pile fabric fastening means 42 extending along the inside of the wearer's left side of panel 32 cooperates with a Velcro strip 43 extending along the outside of the wearer's leftside panel 35. Each of slits 38–41 may be closed in the same fashion. A U-shaped area at the upper end of each of slits 38–41 is preferably reinforced, as by means of double-stitching, such reinforced areas being shown at 38a–41a. When the garment is fully installed on the patient, rods 15–18 of the halo extend through the reinforced areas. The cooperative fastening means provided along the edges of slitfs 38–41 extend from just below the reinforced areas at the upper end of the slits substantially downwardly, preferably to the lower extremities of each slit. It is not necessary, however, that the fastening means extend entirely to the bottoms of the slits in some types of garments; for example, the slits need not be fastened below the belt-line of a man's shirt. While I prefer to use longitudinally-distributed pressure-responsive cooperative fastening means, such as Velcro loop-forming pile fabric connector strips to close slits 38–41, a variety of other cooperative fastening means may be substituted, such as zippers, snap fasteners, or buttons.

The wear of the halo is not able to don the garment himself; it must be placed on him by an assistant. With front opening 30 unbuttoned, the entire garment is first placed adjacent the patient's neck, and the collar made to encircle the patient's neck. Then opening a pair of slits on one side of the garment allows the side panel and front panel on that side of the garment to be trained down that side of the patient's body, and allows an arm of the patient to be inserted into the sleeve, or sleeve opening. For example, with right-side slits 38 and 41 opened, panels 31 and 36 may be trained down the right side of the patient's body, so that rear rightside rod 18 lies adjacent the upper end of rear rightside slit 41 and front rightside rod 15 lies adjacent the upper end of front rightside slit 38. Slits 38 and 41 then can be closed. Then the left side of the garment can be placed on the patient in similar fashion.

It is important to note that the halo device is symmetrical in front-to-rear and left-to-right senses, i.e. that it has two rods in the front and two in the rear. It should become apparent upon reflection, that when a helper places the garment around the neck of the patient preparatory to fully installing it, the mechanics of installing the garment would not be materially different if the patient's head were facing in the opposite direction. Thus it should now become apparent that the invention is applicable not only to garments having a full-length (neck to bottom) opening generally extending down the middle of the front chest line of the wearer, but also applicable to garments having a full-length opening generally extending down the middle of the back of the wearer, such as a "button-up-the-back" blouse. In the preceding description, the term "front" is used to mean the location of the full-length opening, recognizing that in some applications of the invention the front portions of a garment may be located on the back of the wearer.

Figure 6:
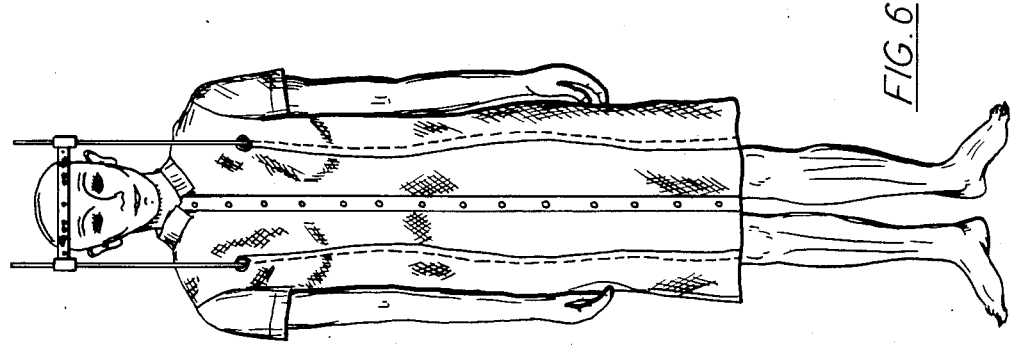
FIG. 6 is a front view of a person wearing a halo and a dress.

It will be apparent from FIG. 6 that construction of a dress in accordance with the invention need differ from the shirt construction already described only in that the panel portions and cooperative fastening means must be longer.

While partial sleeves have been shown on the garment of FIGS. 1 and 2, it will be appreciated that full-length sleeves may be provided, or indeed, no sleeves at all. Similarly, a variety of different forms of collar can be used, or no collar, if desired.

Because typical women's blouses differ from men's shirts almost solely in terms of minor details of styling, it now will be readily apparent that the invention is also applicable to women's blouses. Further, it will be apparent that the upper-torso garment of the invention may be fabricated from a variety of different weights of materials, and that the yoke and the panels can be lined, if desired, so that the invention is readily applicable to a wide variety of jackets.

The invention may be readily applied to underwear, such as men's T-shirts, as well as dress shirts, suit coats, and even overcoats, and hence a plurality of garments can be installed one over the other on the halo wearer.

It will thus be seen that the objects set forth above, among those made apparent from the preceding description, are efficiently attained, and since certain changes may be made in the above construction without departing from the scope of the invention, it is intended that all matter contained in the above description or shown in the accompanying drawings shall be interpreted as illustrative and not in a limiting sense.

The embodiments of the invention in which an exclusive property or privilege is claimed are defined as follows:

1. An upper-torso garment adapted to be worn by a person wearing a cervical traction assembly, said garment comprising, in combination: a neck-encircling upper portion having a pair of front panel portions attached thereto and descending therefrom, and first cooperative fastening means extending along first edges of said front panel portions to allow said front panel portions to be detachably fastened together; a pair of side panel portions and a back panel portion attached to and descending from said neck-encircling portion; and a plurality of further cooperative fastening means extending along the edges of said side panel portions and said back panel portion to allow said back panel portion to be detachably fastened to first edges of said side panel portions and to allow second edges of said side panel portions to be detachably fastened to second edges of said front panel portions.

2. The garment of claim 1 wherein said first cooperaring fastening means comprises cooperating buttons and buttonholes.

3. The garment of claim 1 wherein said further cooperative fastening means include loop-forming pile fabric connector strips.

4. The garment of claim 1 having reinforcing means located adjacent the upper end of each of said further cooperative fastening means.

* * * * *